United States Patent
Birdwell et al.

(10) Patent No.: US 6,507,635 B2
(45) Date of Patent: Jan. 14, 2003

(54) METHOD AND APPARATUS FOR RADIOGRAPHIC INSPECTION OF AIRCRAFT FUSELAGES

(75) Inventors: Thomas William Birdwell, Middletown, OH (US); Andrew Joseph Galish, West Chester, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/822,130

(22) Filed: Mar. 30, 2001

(65) Prior Publication Data

US 2002/0181653 A1 Dec. 5, 2002

(51) Int. Cl.$^7$ ................................................ G01N 23/04
(52) U.S. Cl. ............................ 378/58; 378/41; 378/57
(58) Field of Search .......................... 378/50, 41, 57, 378/146, 198, 99, 62, 90, 46, 86, 87; 250/65, 106, 253; 73/619, 603, 621

(56) References Cited

U.S. PATENT DOCUMENTS 3,775,612 A * 11/1973 Foster et al.
4,976,136 A   12/1990 Willan .................... 73/40.7
5,083,451 A    1/1992 Kling ..................... 73/49.2
5,090,038 A *  2/1992 Asahina .................. 378/41
5,237,598 A *  8/1993 Albert

* cited by examiner

Primary Examiner—Robert H. Kim
Assistant Examiner—George Wang
(74) Attorney, Agent, or Firm—V. G. Ramaswamy; Pierce Atwood

(57) ABSTRACT

A system and method for radiographic inspection of an aircraft fuselage includes a radiation source located on one side of the fuselage and a plurality of radiation detectors located on another side of the fuselage. The system includes manipulators for moving the radiation source and the radiation detectors in a coordinated fashion. Radiation detected by the radiation detectors is processed to display stereoscopic images of areas of interest of the fuselage. The radiation source and detector positions are manipulated to obtain multiple sets of images from different viewing angles. The multiple sets of images are used to produce the stereoscopic images.

12 Claims, 4 Drawing Sheets

METHOD AND APPARATUS FOR RADIOGRAPHIC INSPECTION OF AIRCRAFT FUSELAGES

BACKGROUND OF THE INVENTION

This invention relates generally to radiographic inspection of aircraft fuselages and more particularly to methods and systems for inspecting aircraft fuselages without a-priori knowledge of interfering structures.

An aircraft fuselage typically comprises a grid of circumferential frame members and longitudinal stringers covered by a skin of lightweight sheet metal. The skin is ordinarily attached to the frame members and stringers by means of rivets or the like. To ensure passenger comfort at high altitudes, aircraft are provided with cabin pressurization systems that produce near sea-level air pressure breathing environments in the aircraft cabin. The application of cabin pressure causes the skin, frame members and stringers to expand slightly. When the pressure is removed, the skin, frame members and stringers return to their normal shape. Although the pressure differentials involved are relatively small, the repeated cycles of stress imposed on the fuselage structure by the pressurization and depressurization sequence that occurs during each flight can lead to fatigue and crack formation. This fatigue damage is often assisted by corrosion of the fuselage structures.

Fatigue cracks by nature can be extremely small in size and difficult to detect. The cracks are normally so small that routine pressurization of the aircraft cabin will not result in detection because the tiny cracks will not cause a detectable pressure loss in the aircraft. The combined effect of corrosion and cyclic stress can also cause looseness around the rivets and/or rivet cracking. If not detected, this condition could result in skin separation from the frame members and stringers.

Traditionally, aircraft fuselage inspection relies largely on visual inspection techniques. These techniques rely heavily on human ability and are limited by ambient lighting conditions, environmental effects, and the inspector's physical and mental limitations such as eye vision corrections, time constraints, mental attitude, concentration and judgment. Furthermore, visual inspection techniques require extensive disassembly of the aircraft. This approach is thus time consuming, labor intensive and expensive.

Radiography is another approach to aircraft fuselage inspection that has been proposed. While this approach can reduce the amount of aircraft disassembly required with traditional visual inspections, internal cabin objects can significantly complicate x-ray images, thereby masking defects and making their identification and quantification more difficult. These objects include overhead bins, bulkheads, air masks, oxygen plumbing, lights, electrical wiring, fasteners, lavatory and galley fixtures and so on. If the precise location of such interfering objects is known, viewing angles can usually be determined to allow the areas of interest to be imaged without interference. Some of these interfering objects are in known fixed positions. Other objects vary significantly in location from one aircraft to another. For example, electrical wiring and oxygen plumbing are flexible in nature and do not assume a fixed location. Thus, without sufficient a-priori knowledge of interfering structure location, it is difficult to plan or predict viewing angles that will avoid interference. In which case, the initial inspection will provide images where the field of view has been obstructed. This requires the affected areas to be re-inspected from another angle and perspective, which leads to additional inspection expense and time.

Accordingly, there is a need for a method and apparatus for radiographic inspection of aircraft fuselages that permits all or most of a fuselage to be accurately inspected without a-priori knowledge of interfering structure locations.

BRIEF SUMMARY OF THE INVENTION

The above-mentioned need is met by the present invention, which provides a system and method for radiographic inspection of an aircraft fuselage. The system includes a radiation source located on one side of the fuselage and a plurality of radiation detectors located on another side of the fuselage. The radiation detectors are located in known positions relative to the radiation source so as to receive radiation from the radiation source at different angles. The system further includes manipulators for moving the radiation source and the radiation detectors in a coordinated fashion. The system processes the radiation detected by the radiation detectors so as to display stereoscopic images of areas of interest of the fuselage. The stereoscopic images are obtained by first irradiating the fuselage and the radiation detectors with the radiation source to detect a first set of images of the fuselage from multiple angles, repositioning the radiation source and the radiation detectors with respect to the fuselage, and then irradiating the fuselage and the radiation detectors with the radiation source to detect a second set of images of the fuselage. The multiple sets of images are used to produce the stereoscopic images.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
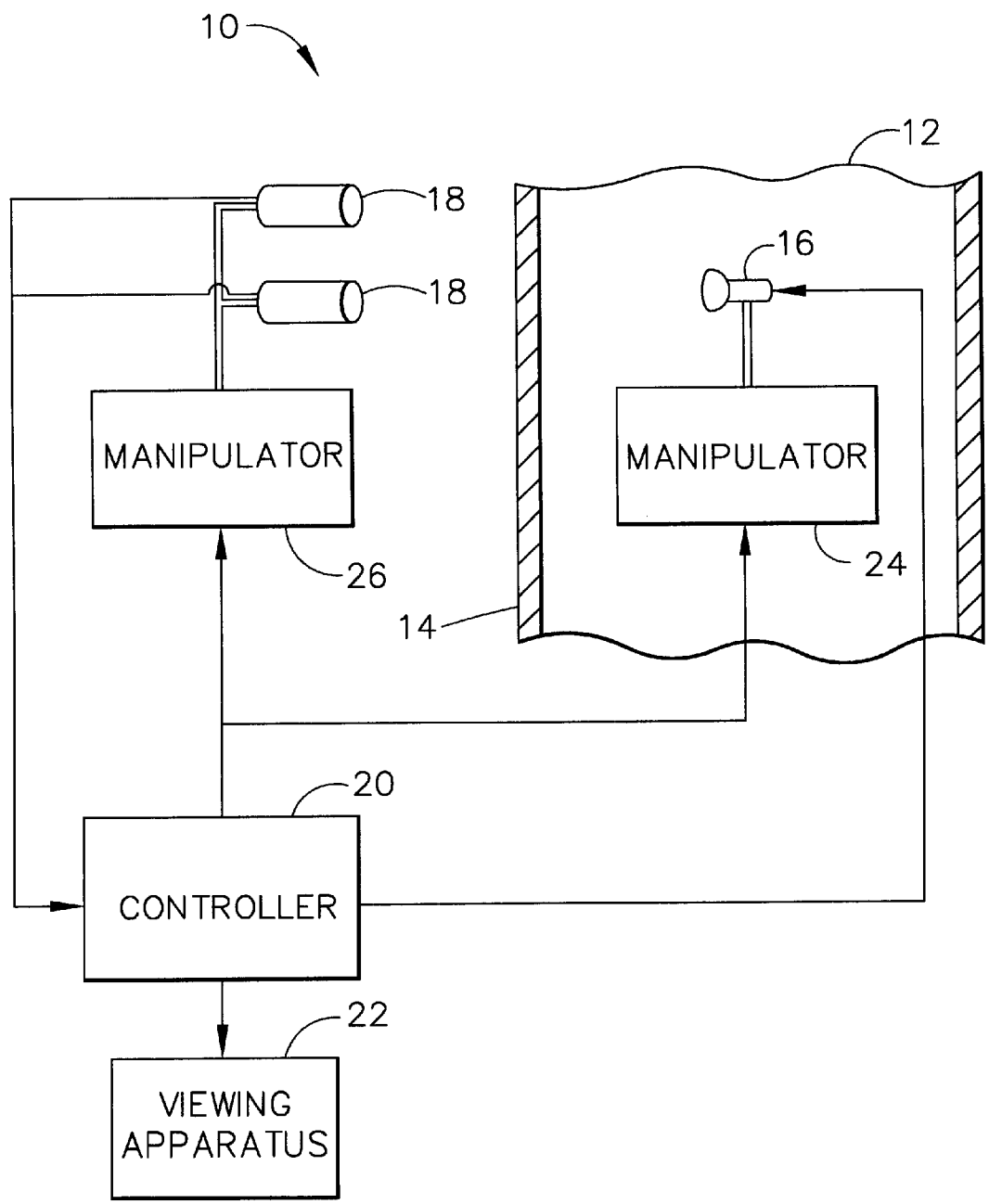
FIG. 1 is a schematic view of a radiographic inspection system for inspecting aircraft fuselages.

Referring to the drawings wherein identical reference numerals denote the same elements throughout the various views, FIG. 1 schematically shows a radiographic inspection system 10 for inspecting an aircraft fuselage 12. The fuselage 12 generally comprises a cylindrical wall 14 made up of a grid of circumferential frame members and longitudinal stringers covered by a skin of lightweight sheet metal. The system 10 includes a radiation source 16 located on a first side of the fuselage wall 14 and a plurality of radiation detectors 18 located on a second, opposite side of the fuselage wall 14. Although two such radiation detectors are shown in FIG. 1, the present invention encompasses more than two detectors, as will become apparent. The radiation source 16 and radiation detectors 18 are relatively situated on opposite sides of the wall 14 so that radiation emitted by the radiation source 16 irradiates the fuselage wall 14 and then impinges on each of the radiation detectors 18. The radiation detectors 18 are positioned relative to the radiation source 16 such that the radiation impinges on each one at a different angle. As shown in FIG. 1, the radiation source 16 is located inside of the fuselage 12, and the radiation detectors 18 are located outside of the fuselage 12. However, it should be noted that this arrangement could alternatively be reversed so that the radiation source 16 is outside and the radiation detectors 18 are inside the fuselage 12.

The radiation source 16 is preferably, but not necessarily, a standard industrial x-ray tube powered by a high voltage power supply (not shown). Alternative radiation sources, such as an isotopic radiation source producing gamma rays, could be used as well. The radiation source 16 provides flux to a large cone-shaped or panoramic volume, but is collimated to limit this to a specific area of interest. Specifically, this zone is made large enough to expose at least two inspection areas (i.e., an inspection area for each detector) at different angles with respect to the source flux axis. The radiation detectors 18 can be any means that is capable of processing radiation emitted by the radiation source 16 into a viewable image. Although x-ray film could be used, it is generally, but not necessarily, preferred that the radiation detector 18 be of the type that converts impinging radiation into an electrical output signal. Many suitable x-ray detectors are commercially available. As is known in the art, such x-ray detectors generally have an x-ray sensitive area and means for producing an output signal that is indicative of the x-rays impinging on the sensitive area.

The image data signals output by the radiation detector 18 are fed to a controller 20, which can be a conventional computer unit. The controller 20 processes these signals and causes corresponding stereoscopic images to be displayed on a viewing apparatus 22, as will be described in more detail below. An operator is then able to view the displayed images to inspect for defects in the fuselage 12. The data image signals are also stored in a memory in the controller 20. The controller 20 also controls the operation of the radiation source 16, turning it on and off and regulating the voltage applied.

Figure 2:
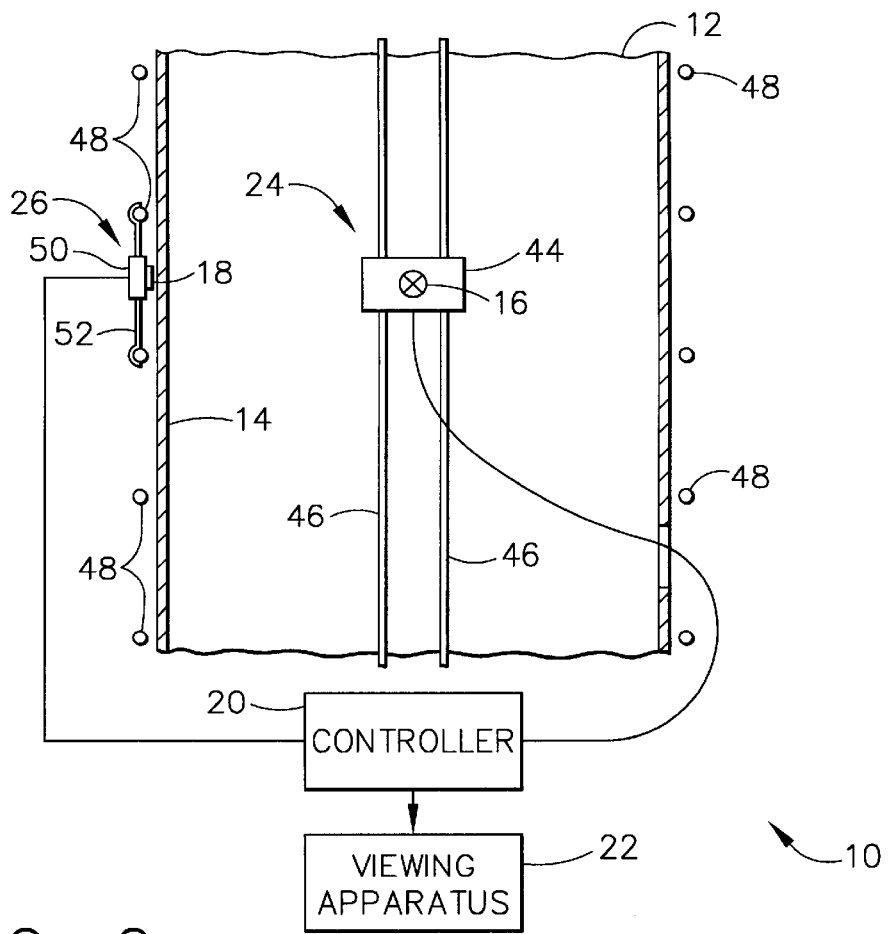
FIG. 2 is a more detailed schematic view of a radiographic inspection system for inspecting aircraft fuselages.
Figure 3:
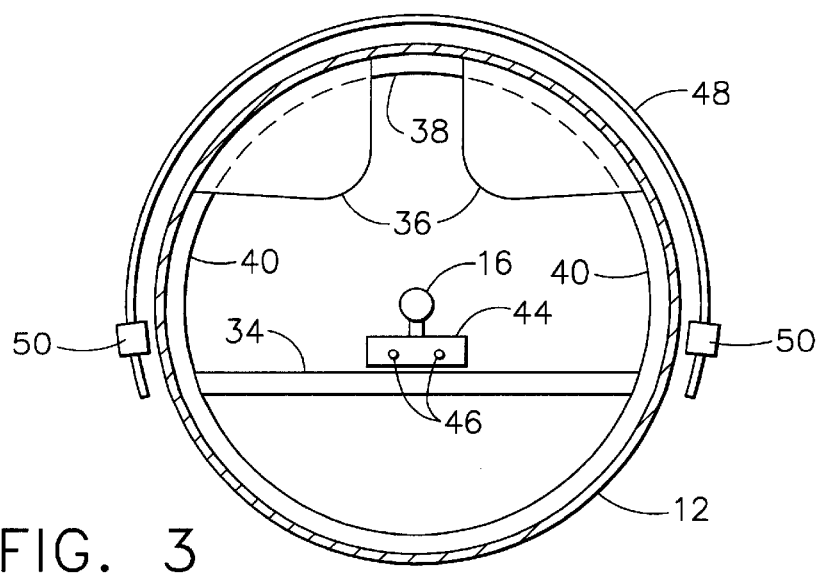
FIG. 3 is a sectional end view of a portion of the radiographic inspection system of FIG. 2.
Figure 4:
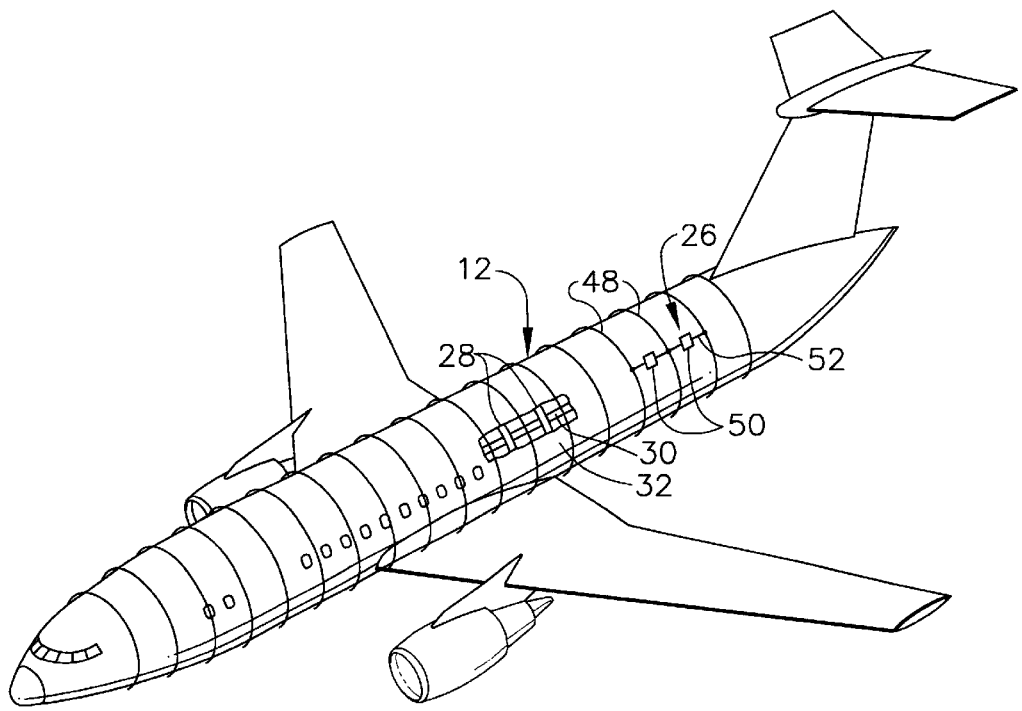
FIG. 4 is a perspective view of an aircraft equipped with the inspection system of FIG. 2 and having a portion of the fuselage shown in partial cutaway to reveal internal fuselage structure.

A first precise manipulator 24 is provided for moving the radiation source 16 with respect to the fuselage 12, and a second precise manipulator 26 is provided for moving the radiation detector 18 with respect to the fuselage 12. The precise manipulators 24, 26 can be any type of device capable of producing the desired motion. This would include robotic devices, guide rail systems and the like. One suitable manipulator arrangement is shown in FIGS. 2–4 in which the fuselage wall 14 is made up of a grid of circumferential frame members 28 and longitudinal stringers 30 (shown in cutaway in FIG. 4) covered by a skin 32 of lightweight sheet metal. As seen in FIG. 3, a passenger deck 34 is disposed horizontally in the fuselage 12 so as to define the floor of an interior cabin. The cabin can be provided with conventional overhead bins 36, ventilation panels 38 and side panels 40. Although not shown in the Figures, the fuselage 12 typically includes other conventional structure such as lights, wiring, insulation and the like.

The first manipulator 24 includes a first carrier 44 to which the radiation source 16 is mounted. The first carrier 44 is slidingly mounted on two linear guide rails 46 that are disposed on the passenger deck 34 and extend parallel to the center longitudinal line of the fuselage 12. The first carrier 44 is moved back and forth along the guide rails 46 under the control of the controller 20. The motion is produced by any conventional motive means such as an electric motor (not shown) in a manner known in the art. Thus, the radiation source 16 can be selectively positioned along the length of the fuselage 12. With this arrangement, the radiation source 16 is collimated to produce a panoramic radiation beam in the circumferential direction of the fuselage 12, but limited in the forward and aft directions to the specific area of interest. The radiation source 16 thus illuminates the fuselage 12 from floor line to floor line above the passenger deck 34 along a relatively short longitudinal section of the fuselage 12.

The first manipulator 24 is configured to move the radiation source 16 through the desired range of motion without interference with any objects located inside the fuselage 12. Accordingly, such objects (which may include overhead bins, bulkheads, air masks, oxygen plumbing, lights, electrical wiring, fasteners, lavatory and galley fixtures, etc.) need not be removed to perform an inspection.

The second manipulator 26 utilizes a rail system that includes a plurality of curved guide rails 48 mounted to the outer surface of the fuselage 12. Mounting can be accomplished by any means such as suction cups fixed to the rails 48 and engaging the fuselage 12. The guide rails 48 are oriented circumferentially with respect to the fuselage 12 and are spaced out along the length of fuselage 12. Each guide rail 48 is configured to match the fuselage curvature and extends from a point adjacent to the passenger deck 34 on one side of the fuselage 12, over the fuselage crown, and to a point adjacent to the passenger deck 34 on other side of the fuselage 12. The guide rails 48 are thus arranged to track the path of the panoramic radiation beam emitted by the radiation source 16. The curved guide rails 48 are situated on the fuselage 12 so as to position the radiation detectors 18 over the areas of interest of the fuselage 12. Each radiation detector 18 is mounted between a respective pair of adjacent guide rails 48, and each pair of adjacent guides rails 48 defines a inspection area of interest. The guide rails 48 are accordingly located on opposing sides of the fuselage structure to be inspected. For example, FIG. 4 shows the guide rails 48 straddling respective ones of the frame members 28 so that they can be inspected for defects. However, it should be noted that the system 10 could also be used for inspecting other fuselage structure such as stringers, lap joints and the like. The guide rails 48 would simply be positioned accordingly.

The second manipulator 26 includes a second carrier 50 for each radiation detector 18 and a support beam 52 that supports each of the second carriers 50. Two radiation detectors 18 are shown in FIGS. 2–4, but as previously mentioned, more than two detectors can be employed. Each radiation detector 18 is mounted to the underside of the second carrier 50 so as to face the fuselage 12. The support beam 52 is slidingly mounted on the adjacent guide rails 48 defining the selected inspection areas so as to locate the radiation detectors 18 at the desired locations with respect to the fuselage 12. The support beam 52 is moved along the selected guide rails 48 under the control of the controller 20 by any conventional motive means in a manner known in the art. Thus, the radiation detectors 18 are capable of traveling over the outer surface of the fuselage 12 above the passenger deck 34. The controller 20 moves the carriers 44 and 50, and thus the radiation source 16 and radiation detectors 18, in a coordinated fashion such that the radiation detectors 18 are precisely located relative to the radiation source 16.

Figure 5:
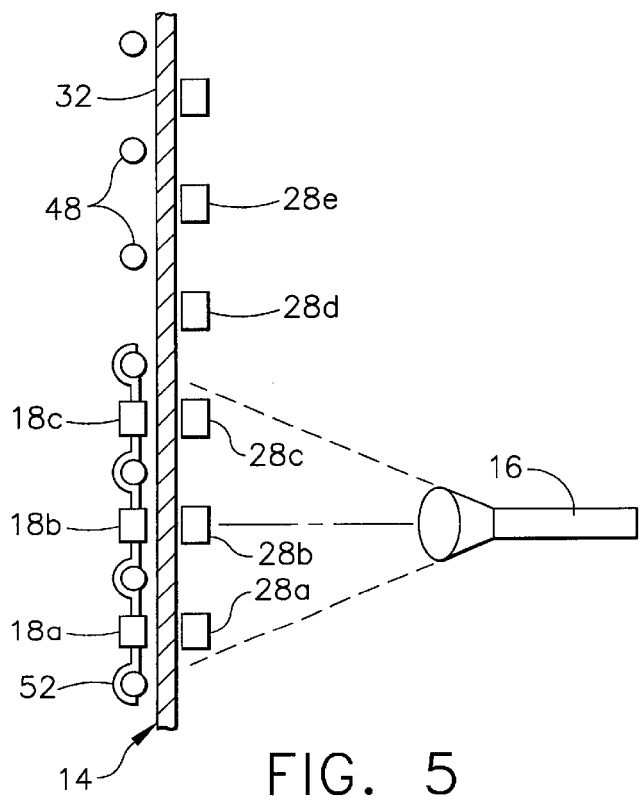
FIG. 5 is a partial schematic view of the radiographic inspection system with the radiation source and detectors in a first position.

The operation of the inspection system 10 is now described with reference to FIGS. 5–7, which, by way of example, depict the inspection of a portion of the fuselage wall 14 that encompasses a series of adjacent frame members denoted by reference numerals 28a–28e. In the illustrated example, three radiation detectors 18a–18c are mounted on the curved guide rails 48 of three selected inspection areas, although it should be noted that the present invention is not limited to this particular number of detectors. Furthermore, the present invention is not limited to inspecting frame members and can be used for inspecting other fuselage structure such as stringers, lap joints and the like. As shown in FIG. 5, the detectors 18a–18c are arranged so that detector 18a is aligned with frame member 28a, detector 18b is aligned with frame member 28b, and detector 18c is aligned with frame member 28c. The first manipulator 24 is controlled to move the radiation source 16 into longitudinal alignment with the center detector 18b so that each of the three detectors 18a–18c will be exposed to radiation from the radiation source 16, albeit at different angles.

The radiation source 16 is then turned on so that the adjoining region of the fuselage 12 above the passenger deck 34 is illuminated with radiation. While the radiation source 16 is emitting radiation, the second manipulator 26 is activated to cause the radiation detectors 18a–18c to travel over the outer surface of the fuselage 12. Radiation emitted by the radiation source 16 passes through the frame members 28a–28c and impinges on the corresponding one of the radiation detectors 18a–18c. The radiation is converted into electrical signals that are fed to the controller 20. Thus, detector 18a detects an image of frame member 28a at a first angle, detector 18b detects an image of frame member 28b at a second angle (perpendicular to the longitudinal axis of the fuselage 12), and detector 18c detects an image of frame member 28c at a third angle.

Figure 6:
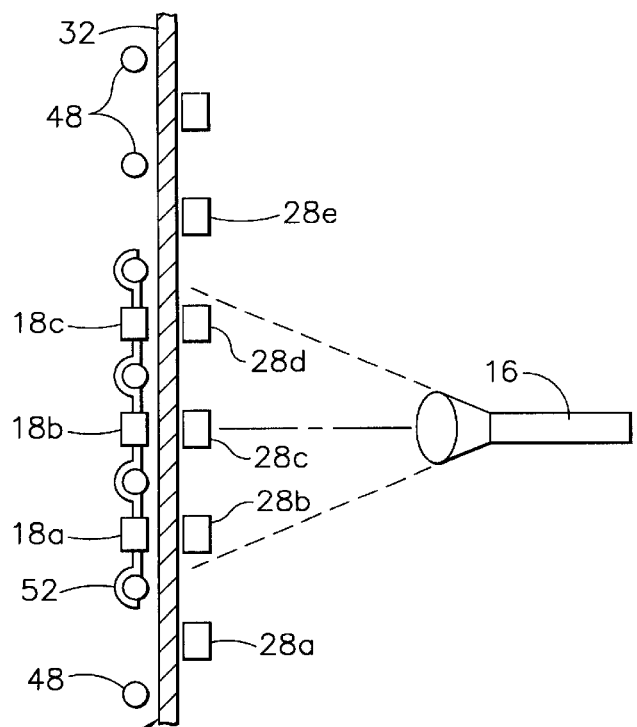
FIG. 6 is a partial schematic view of the radiographic inspection system with the radiation source and detectors in a second position.

Once the inspection of the fuselage 12 at the first position is completed, the radiation detectors 18a–18c are repositioned on the fuselage 12 so that detector 18a is aligned with frame member 28b, detector 18b is aligned with frame member 28c, and detector 18c is aligned with frame member 28d, as shown in FIG. 6. The first manipulator 24 again moves the radiation source 16 into longitudinal alignment with the repositioned center detector 18b and frame member 28c. The inspection at this position is then carried out in the same manner with the radiation detectors 18a–18c being moved over the outer surface of the fuselage 12 while the radiation source 16 is turned on. In this position, detector 18a detects an image of frame member 28b at the first angle, detector 18b detects an image of frame member 28c at the second angle, and detector 18c detects an image of frame member 28d at the third angle.

Figure 7:
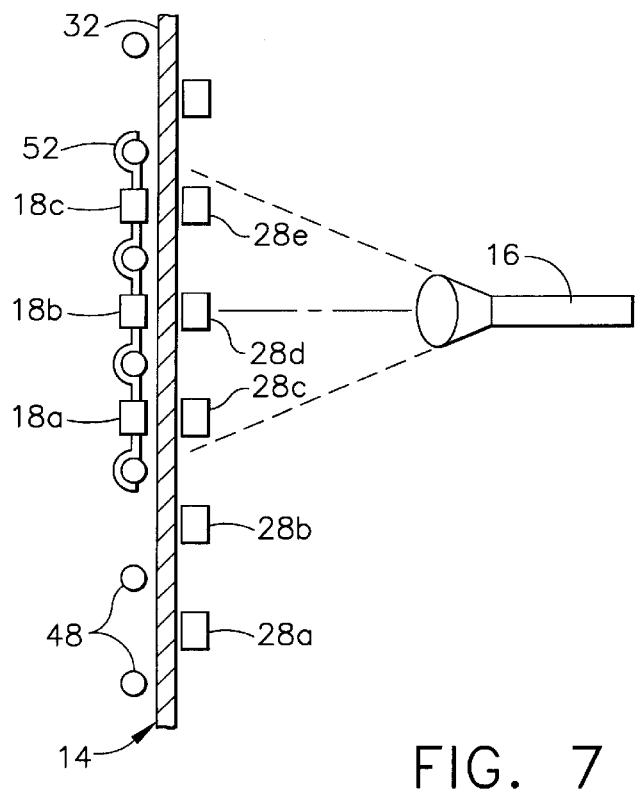
FIG. 7 is a partial schematic view of the radiographic inspection system with the radiation source and detectors in a third position.

Next, the radiation detectors 18a–18c are again repositioned on the fuselage 12, as shown in FIG. 7, so that detector 18a is aligned with frame member 28c, detector 18b is aligned with frame member 28d, and detector 18c is aligned with frame member 28e. The first manipulator 24 again moves the radiation source 16 into longitudinal alignment with the repositioned center detector 18b. Inspection at this position is then carried out in the same manner with the radiation detectors 18a–18c being moved over the outer surface of the fuselage 12 while the radiation source 16 is turned on. In this position, detector 18a detects an image of frame member 28c at the first angle, detector 18b detects an image of frame member 28d at the second angle, and detector 18c detects an image of frame member 28e at the third angle. This process is repeated sequentially down the length of the fuselage 12 until each frame member has been imaged from each of the three angles.

The controller 20 processes the various signals from the detectors 18a–18c for display on the viewing apparatus 22. Since the images are taken at a precise and known geometry, the viewing apparatus 22 will permit an operator to view the images in a stereoscopic manner. A wide variety of electro-optical viewing apparatuses for presenting stereoscopic images are commercially available. In the event that film is used instead of electronic detectors, numerous mechanical stereoscopic viewing devices are also available. By providing multiple viewing angles of each frame member, the inspection system 10 allows for depth perception in the images. That is, an operator will be able to distinguish the different geometrical depths of the frame members and overlapping structures such as overhead bins, bulkheads, air masks, oxygen plumbing, lights, electrical wiring, and the like. The operator will thus be able to discern defects in the frame members from image artifacts caused by interfering structure located between the radiation source and the frame members. This will also enable determination of the depth location of defects within the frame members. Furthermore, known digital image techniques can be used to enhance the images.

The foregoing has described a method and apparatus for radiographic inspection of aircraft fuselages that permits all or most of a fuselage to be accurately inspected without a-priori knowledge of interfering structure locations. While specific embodiments of the present invention have been described, it will be apparent to those skilled in the art that various modifications thereto can be made without departing from the spirit and scope of the invention as defined in the appended claims.

What is claimed is:

1. A system for radiographic inspection of an aircraft fuselage, said system comprising:

a radiation source located on one side of said fuselage; a plurality of radiation detectors located on another side of said fuselage, said radiation detectors being positioned to receive radiation from said radiation source at different angles;

means for moving said radiation source and said radiation detectors in a coordinated fashion so that each radiation detector is able to detect multiple images of a particular area of said fuselage from multiple viewing angles, said means for moving said radiation source and said radiation detectors comprising a first manipulator for moving said radiation source and a second manipulator for moving said radiation detectors, said first manipulator comprising at least one guide rail disposed inside said fuselage and extending longitudinally with respect to said fuselage and a carrier slidingly mounted on said guide rail, said radiation source being mounted on said carrier; and means for displaying stereoscopic images based on output from said radiation detectors.

2. The system of claim 1 further comprising a controller for controlling said first and second manipulators.

3. The system of claim 1 wherein said first manipulator moves said radiation source without interference with any objects in said fuselage.

4. The system of claim 1 wherein said second manipulator comprises a plurality of guide rails mounted to an outer surface of said fuselage and a plurality of carriers slidingly mounted between adjacent ones of said guide rails, each one of said radiation detectors being mounted on one of said carriers.

5. The system of claim 4 wherein said second manipulator further comprises a support beam slidingly mounted to a group of said guide rails, said carriers being mounted to said support beam.

6. The system of claim 1 wherein said radiation source is an x-ray source and said radiation detectors are x-ray detectors.

7. A system for radiographic inspection of an aircraft fuselage, said system comprising:

a radiation source located on one side of said fuselage;

a plurality of radiation detectors located on another side of said fuselage, said radiation detectors being located in known positions relative to said radiation source so as to receive radiation from said radiation source at different angles;

means for moving said radiation source and said radiation detectors in a coordinated fashion so that each radiation detector is able to detect multiple images of a particular area of said fuselage from multiple viewing angles, said means for moving said radiation source and said radiation detectors comprising a first manipulator for moving said radiation source and a second manipulator for moving said radiation detectors, said first manipulator comprising at least one guide rail disposed inside said fuselage and extending longitudinally with respect to said fuselage and a carrier slidingly mounted on said guide rail, said radiation source being mounted on said carrier;

means for processing radiation detected by said radiation detectors so as to produce stereoscopic images of areas of interest of said fuselage; and means for displaying said stereoscopic images.

8. The system of claim 7 further comprising a controller for controlling said first and second manipulators.

9. The system of claim 7 wherein said first manipulator moves said radiation source without interference with any objects in said fuselage.

10. The system of claim 7 wherein said second manipulator comprises a plurality of guide rails mounted to an outer surface of said fuselage and a plurality of carriers slidingly mounted between adjacent ones of said guide rails, each one of said radiation detectors being mounted on one of said carriers.

11. The system of claim 10 wherein said second manipulator further comprises a support beam slidingly mounted to a group of said guide rails, said carriers being mounted to said support beam.

12. The system of claim 7 wherein said radiation source is an x-ray source and said radiation detectors are x-ray detectors.

* * * * *